United States Patent

Cabre et al.

[11] Patent Number: 5,990,351
[45] Date of Patent: Nov. 23, 1999

[54] PROCESS FOR SEPARATING PIVALIC ACID FROM SPENT REACTION MIXTURES

[75] Inventors: Joan Cabre; Victor Centellas; Jose Diago; Asuncion Esteve; Joan Serrat, all of Barcelona, Spain

[73] Assignee: Biochemie GmbH, Austria

[21] Appl. No.: 08/981,572

[22] Filed: Dec. 22, 1997

[30] Foreign Application Priority Data

Jun. 28, 1995 [GB] United Kingdom .................... 9513115

[51] Int. Cl.$^6$ .......................... C07C 53/128; C07C 51/60
[52] U.S. Cl. ............................................. 562/606; 562/840
[58] Field of Search ...................... 562/606, 840

[56] References Cited

U.S. PATENT DOCUMENTS

| | | | |
|---|---|---|---|
| 2,255,421 | 9/1941 | Groll et al. | 562/531 |
| 4,770,821 | 9/1988 | Miyazawa et al. | 562/864 |
| 5,202,462 | 4/1993 | Yazawa et al. | 560/236 |

FOREIGN PATENT DOCUMENTS

| | | |
|---|---|---|
| 0 439 096 | 7/1991 | European Pat. Off. . |
| 850176 | 9/1960 | United Kingdom . |
| 2176184 | 12/1986 | United Kingdom . |

OTHER PUBLICATIONS

Aldrich Chemical Company Catalog, p. 1480, 1996.
Alfa Catalog Research Chemicals and Accessories, p. 405, 1993–1994.

*Primary Examiner*—Rosalynd Keys
*Attorney, Agent, or Firm*—Lydia T. McNally

[57] ABSTRACT

A process for recovering 2,2-dimethylpropanoic acid in highly pure form from a mixture of 2,2-dimethylpropanoic acid and impurities which may be obtained in the production of a beta lactam antibiotic, by degrading impurities and separating off the volatile fragments.

7 Claims, No Drawings

PROCESS FOR SEPARATING PIVALIC ACID FROM SPENT REACTION MIXTURES

This invention relates to a process for separating pivalic acid, also known as 2,2-dimethylpropanoic acid, from spent reaction mixtures.

Pivalic acid is used in a number of highly efficient chemical production processes, often in the form of reactive derivatives thereof, e.g. mixed anhydrides. At the end of reaction a spent reaction mixture may be obtained containing pivalic acid, for example a mixture containing pivalic acid with degradable impurities. Pivalic acid as used herein is understood to include a derivative of pivalic acid easily convertible into pivalic acid. Up till now little has been published on the recovery of pivalic acid in sufficiently acceptable purity for further use from spent reaction mixtures on economical commercial scale.

One such production process, wherein pivalic acid is obtained in the spent reaction mixture, is the production of beta lactam antibiotics, for example 6-alpha-aminoacyl-penicillins and 7-alpha-aminoacyl-(desacetoxy)-cephalosporins, such as ampicillin, amoxicillin, cephalexin, cefadroxil and cephradine, using pivalic acid mixed anhydrides in any of a wide range of solvent systems. These may be obtained, for example, by a process described in EP 439 096 or EP 523 585. In such a process 6-aminopenicillanic acid (6-APA) or 7-amino-desacetoxy-cephalosporanic acid (7-ADCA) may be acylated with the corresponding side chain, which may be, for example, a phenylglycine group. The reaction goes in very good yields.

The amine group of, for example a phenylglycine is generally temporarily protected by formation of the corresponding enamine, formed, for example, by reaction with an alkyl acetoacetate, such as methyl or ethylacetoacetate, in the presence of a base. These protected compounds have a general formula

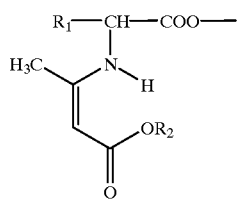

I wherein $R_1$ denotes an appropriate side chain, e.g. phenyl, 4-hydroxyphenyl or 1,4-cyclohexadien-1-yl and $R_2$ denotes, for example, alkyl, preferably $C_{1-8}$alkyl, for example $C_{1-4}$alkyl, such as methyl or ethyl. The amine group and the carbonyl group are attached to the double bond preferably in the cis configuration. Such a compound is advantageously used in the form of a salt, preferably in the form of a potassium or sodium salt, known and readily available under the generic name "Dane salt".

The Dane salt may be reacted with pivaloyl chloride, optionally in the presence of pivalic acid, to give a mixed anhydride of formula

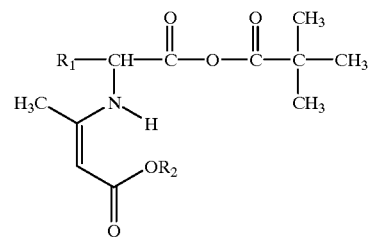

II wherein $R_1$ and $R_2$ are as defined above.

In the acylation step generally about 1.05 to 1.2 mole of a compound of formula II per mole of 6-APA or 7-ADCA is used. This means, per kg of 6-APA or 7-ADCA about 0.5 to 0.6 kg of pivalic acid are formed during the acylation step. Further pivalic acid may be already present as an additional component in the reaction mixture to improve yields. The amine group of the acylated product is then deprotected, for example by hydrolysis of the enamine moiety. The corresponding alkyl acetoacetate is set free. The beta lactam is isolated and the spent reaction mixture containing pivalic acid and an alkyl acetoacetate is left.

It is highly desirable to recycle as much as possible from the spent reaction mixture. If a biphasic system is produced both pivalic acid and alkyl acetoacetate are present in the organic layer.

The spent reaction mixture, for example a mixture of pivalic acid with degradable impurities, may contain further components, for example the solvent or solvent mixture used in the synthesis of the beta lactam antibiotic, as well as by products.

Solvents include hydrocarbons, optionally halogenated, for example methylene chloride, ketones, such as acetone, methyl isobutylketone, esters, such as ethylacetate, isopropylacetate, n-butylacetate, water or mixtures thereof. By-products include 2-ethylhexanoic acid, often present in the preparation of the mixed anhydride and/or in the acylation step pivalamide of the acid 6-aminopenicillanic acid (6-APA) or 7-ADCA, typical by-product formed in the reaction of the mixed anhydride with pivaloyl chloride N-pivaloyl phenylglycines, formed for example, from the excess of mixed anhydride in the hydrolysis step penicillins or cephalosporins partially extracted in the organic layer penicilloic or penilloic acids, or corresponding cephalosporanic equivalents thereof, formed for example by hydrolysis of the beta lactam ring.

Generally a residue, often oily, is obtained after isolation of the desired product, for example a beta lactam antibiotic, which contains pivalic acid. Spent reaction mixtures may be collected from the production of different beta lactam antibiotics; so the mixture may contain many components, often closely related, e.g. methyl and ethyl acetoacetate. Recovery of solvents and other volatile components may be effected by (fractionated) distillation under normal or reduced pressure of spent reaction mixtures. However, it has not been possible to produce a pivalic acid containing fraction which can be used further as such. We have effected detailed analysis of typical pivalic acid containing fractions. These contain considerable amounts of impurities. Thus, methyl acetoacetate (bpt: 169°) and/or ethyl acetoacetate (bpt: 158°) is difficult to separate economically from pivalic acid (bpt: 164°).

Pivalic acid recovery would improve the economics of operating an overall process, for example a beta lactam antibiotic process, wherein pivalic acid remains in the spent reaction mixture and would be advantageous from the environmental view point. Thus, on one hand pivalic acid recovered as such can be easily converted into pivaloyl chloride, which may be used in the preparation of further beta lactam antibiotic. Also recovery of pivalic acid reduces on the other hand at the same time (oily) residues, obtained after solvent recovery, which would have to be disposed, e.g. incinerated.

Attempts to recover pivalic acid on an economical industrial scale from mixtures as described above have so far failed. There is therefore a need for a commercially acceptable process for the separation and recovery of pivalic acid in good yields and purities.

This invention provides a process for recovering pivalic acid having a number of significant and economical advantages on industrial scale. Pivalic acid present in the mixture after isolating the antibiotic is recovered without using any organic solvent, avoiding complicated and unselective extraction steps.

This invention provides in one aspect a process for separating pivalic acid containing a mixture of pivalic acid with degradable impurities which comprises the steps of
 a) degrading impurities to produce volatile fragments
 b) distilling off the volatile fragments; and
 c) isolating the pivalic acid.

In another aspect the present invention provides a process as defined above, wherein the mixture containing pivalic acid with degradable impurities is obtained from the production of a beta lactam, such as ampicillin, amoxicillin, cephalexin, cefadroxil and cephradine, for example from an acylation reaction.

In degradation step a) impurities, for example, alkyl acetoacetates, for example of formula

III

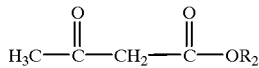

wherein
 $R_2$ is as defined above, in the mixture are degraded to give volatile fragments which may be easily distilled off.

In a further aspect the present invention provides a process as defined above, wherein impurities contain an alkyl acetoacetate.

The degradation products may be, for example, carbon dioxide and acetone. Alkyl acetoacetates are typically degraded to give the corresponding alkanol, carbon dioxide and acetone, according to the following scheme:

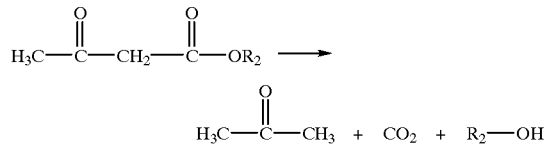

wherein
 $R_2$ is as defined above.

In degradation step a) degradation is preferably carried out by hydrolysis.

In a further aspect the present invention provides a process as described above, characterized in that degradable impurities are degraded by hydrolysis.

Any hydrolysis process may be used according to which degradable impurities, for example alkyl acetoacetates, are degraded without decomposing the pivalic acid. Hydrolysis includes hydrolysis under acidic, basic or neutral conditions or enzymatic hydrolysis. Basic hydrolysis may be carried out e.g. with an alkali at pH of about 9 to 11. Preferably hydrolysis under strong acidic conditions may be used. Suitable acids include inorganic and organic acids or acidic ion exchange resins, preferably inorganic acids, such as hydrochloric acid, and especially sulfuric acid, e.g. at pH from about 0.05 to 1. Preferably an aqueous suspension or preferably solution of an acid may be used.

In a further aspect the present invention provides a process as defined above, comprising hydrolysis is carried out under strong acidic conditions.

Degradation may be carried out, e.g. at room temperature or elevated temperatures but lower than the pivalic acid boiling point (164°).

It is preferred to effect this degradation step a) simultaneously with distillation step b), for example by heating during step a).

Thus the mixture being treated in step a), e.g. the mixture may be heated, to cause distillation of the degradation products in a stripping process and the degradation may proceed faster.

In a further aspect the present invention provides a process as described above, wherein step a) and step b) are carried out simultaneously by heating during step a).

Distillation step b) may be effected at temperatures which do not cause distilling off of pivalic acid, e.g. below 164°, such as temperatures up to 13°, preferably from 50 to 120°, more preferably from 80 to 110°.

A vacuum, e.g. from 10 to 50 mm Hg (using lower appropriate temperatures) may be used, if desired.

Isolation step c) may be simply effected by cooling the mixture after distillation. A biphasic system may be formed, optionally when the mixture is cooled. The upper layer in such a biphasic system contains almost pure pivalic acid, the lower layer the aqueous, especially acidic, solution and optionally some dissolved pivalic acid. Derivatives of pivalic acid, e.g. salts optionally produced after alkaline or neutral hydrolysis, may be converted into the free acid by acidification, e.g. with hydrochloric acid, optionally to form the biphasic system. It is surprising that the pivalic acid forms an upper layer, which can be easily separated off, e.g. by decantation, to produce pivalic acid in acceptable quality for further use.

The pivalic acid thus obtained is obtained in high yields, generally in yields of more than 80%, particularly even above 90% based on the amount of pivalic acid present in the mixture before degradation step a).

The lower layer may be used for further recovery processes to recover pivalic acid or, if acidic, as an acid phase for degradation in step a).

In another aspect the present invention provides a process for separating pivalic acid from a spent reaction mixture containing pivalic acid and an alkyl acetoacetate obtained in the production of a beta lactam, characterized by the steps
 (i) distilling the spent reaction mixture to produce a fraction containing a mixture of pivalic acid and an alkyl acetoacetate,
 (ii) degrading an alkyl acetoacetate in the fraction obtained in step (i) by hydrolysis to produce volatile fragments
 (iii) distilling off the volatile fragments optionally simultaneously with step (ii); and
 (iv) isolating the pivalic acid.

The pivalic acid is obtained in high purity of more than 90%, for example even above 97% or 98%, the main impurity may be water. Alkyl acetoacetate is present, albeit in trace amounts, detectable, for example by gas chromatography, e.g. from 0.001 to 0.01%, not present in commercially available pivalic acid. Such a pivalic acid composition is novel and forms part of this invention.

In another aspect the invention provides a pivalic acid composition containing as an impurity an alkyl acetoacetate and water, the alkyl acetoacetate content being less than 0.01% and the water content from 0.05 to 2%.

The pivalic acid composition is highly useful, even in liquid form, and can be further used as such, optionally after drying, for example for the preparation of pivaloyl chloride, for example by reaction with thionyl chloride or phosgene, which may be used again in the preparation of the mixed anhydride as described above. The pivalic acid composition may also be used as a component as such in beta lactam antibiotic production to increase yields.

In a further aspect the present invention provides the use of pivalic acid obtained by the process of the invention in the production of pivaloyl chloride.

The origin of the starting mixture for degradation step a) is not critical. Conveniently it contains at least 40% pivalic acid. Conveniently the starting mixture for step a) is a distillate, e.g. obtained by fractionally distilling a spent reaction mixture (optionally after recovering the solvents), e.g. produced from beta lactam acylation, e.g. carried out in methylene chloride or methylene chloride free solvent systems, to produce a fraction containing pivalic acid. Such distillation of a spent reaction mixture containing pivalic acid and impurities, for example alkyl acetoacetates, separates the pivalic acid from by-products of higher boiling point.

In a further aspect the present invention provides a process as defined above, wherein the mixture of pivalic acid with degradable impurities is obtained by distilling a spent reaction mixture produced from beta lactam acylation reaction to produce a fraction containing the mixture of pivalic acid and impurities.

Preferably a fraction is produced containing at least 50% pivalic acid, the reminder being substantially alkyl acetoacetate. Optionally other volatile components may be present. This may be effected in vacuo, e.g. from 5 to 13 mm Hg. Such a composition is new.

In a further aspect the present invention provides therefore a composition containing at least 50% pivalic acid, the reminder being substantially alkyl acetoacetate.

All percentages are by weight (w/w), unless otherwise defined.

The following non-limitative examples illustrate the invention. All temperatures are in degrees Centigrade and are uncorrected.

In the examples the following abbreviations are used
NBA: n-Butyl acetate
MC: Methylene chloride
IA: Isopropyl acetate
PIVA: Pivalic acid
2-EH: 2-Ethylhexanoic acid
EAA: Ethyl Acetoacetate
MAA: Methyl Acetoacetate
NVC: Non volatile compounds Yields are based on pivalic acid in starting mixture for degradation step a). Pivalic acid obtained contains about 0.005% EAA and/or MAA and from 0.05 to 2% water.

EXAMPLE 1

Production of Enriched PIVA/MAA/EAA Mixture

A mixture of 223.3 g of NBA (9.6%), MAA (13.2%), EAA (20.8%), PIVA (42.6%,2-EH (7.2%) and NVC (6.6%) (% by weight), obtained as a distillation bottom in the solvent recovery from the production of semi-synthetic penicillins, is distilled in vacuo. The main fraction, collected at a pressure of 5 to 13 mm Hg and a temperature of 54 to 66° C., contains almost all of the pivalic acid mixed with ethyl and methyl acetoacetates, and has the composition PIVA (55.6%), MAA (17.2%) and EAA (27.2%).

Degradation Step a)/Distillation Step b)

To 51.82 g of the above mentioned main fraction, a mixture of 48 ml water and 2.2 ml concentrated sulfuric acid is added in order to reach a pH value of about 0.1. The acidic mixture is heated to about 98 to 101° for about 90 minutes, the volatile components, basically methanol, ethanol and acetone are stripped off. A biphasic system is formed in the distillation residue, wherein the upper layer is almost pure pivalic acid and the lower layer is acidic water saturated with PIVA.

Isolation Step c)

The upper layer is separated off from the lower layer. 26.8 g of PIVA (93% of theory) are obtained, with a purity of 98.0%. The lower, aqueous layer may be reused as such for further recovery operations as described to replace at least part of the sulfuric acid and water in degradation step a), thus allowing increasing the overall recovery yield.

EXAMPLE 2

Example 1 is repeated with the following changes in degradation step a): 9 ml concentrated hydrochloric acid instead of 2.2 ml concentrated sulfuric acid are used in step b). Yield 92%, purity 98.0%.

EXAMPLE 3

Example 1 is repeated with the following changes in degradation step a) and distillation step b): Stripping off volatile compounds is carried out during hydrolysis, i.e. during addition of water and acid to the mixture, with an overall time of two hours; instead of 90 minutes of hydrolysis followed by stripping. Yield 89%, purity 97.2%.

EXAMPLE 4

Example 1 is repeated with the following changes in degradation step a): 3.0 g of an acidic ion-exchange resin (Amberlyst 15) are used instead of concentrated sulfuric acid. Yield 90%, purity 97.7%.

EXAMPLE 5

Degradation Step a)/Distillation Step b) of a Mixture Containing PIVA (55.9%), MAA (17.2%) and EAA (26.7%)

50.69 g of an enriched fraction obtained as described in Example 1 are treated with a mixture of 73 ml water. 55.3 g of 20% aqueous sodium hydroxide are added. A pH of about 9.6 is achieved. The mixture is heated to about 98 to 101° for about 120 minutes, the volatile components, basically methanol, ethanol and acetone, being stripped off at the same time.

Isolation Step c)

After cooling, the pH of the distillation residue is adjusted to 1.4 by adding hydrochloric acid. A biphasic system is formed in the distillation residue, wherein the upper layer is almost pure pivalic acid and the lower layer is acidic water saturated with PIVA. PIVA is separated off. 24.9 g of PIVA (88% of theory) are obtained. Purity: 98.0%.

EXAMPLE 6

Degradation step a)/Distillation Step b)

A mixture of
i) 50.0 g PIVA (73.9%) and MAA (26.1%) or
ii) 50.8 g PIVA (73.7%) and EAA (26.3%) is treated with water and sulfuric acid to adjust a pH of about 0.8 and heated to 96 to 99° for about 90 minutes, stripping off the volatile components at the same time.

Isolation Step c)

A biphasic system is formed in the distillation residue upon cooling, wherein the upper layer is almost pure pivalic acid and the lower layer is acidic water saturated with PIVA. The upper layer is separated off.

i) 35.9 g of PIVA (97% of theory) are obtained. Purity: 98.0%; or
ii) 35.0 g of PIVA (93% of theory) are obtained. Purity: 97.0%; respectively. The lower, aqueous layer may be reused as described in Example 1.

EXAMPLE 7

Example 1 is repeated, but using a mixture of 76.8 g of IA (2%), PIVA (55.1%), MAA (16.2) % and EAA (26.7%) as enriched PIVA/MAA/EAA mixture instead of the mixture as described in Example 1. 39.8 g of PIVA (94% of theory) are obtained. Purity: 97.9%.

EXAMPLE 8

Example 1 is repeated, but using a mixture of 55.3 g MC (1.5%), PIVA (56.1%), MAA (16.0%) and EAA (26.4%) as enriched PIVA/MAA/EAA mixture instead of the mixture as described in Example 1. 28.5 g of PIVA (92% of theory) are obtained. Purity: 98.0%.

The above examples may be effected on the kilogram scale rather than gram scale (i.e. 1000×scale) with substantially identical results.

We claim:

1. A process for separating pivalic acid from a mixture containing pivalic acid and degradable impurities which comprises
   a) hydrolyzing the impurities to produce volatile fragments;
   b) distilling off the volatile fragments; and
   c) isolating the pivalic acid.

2. A process according to claim 1, wherein the mixture of pivalic acid containing degradable impurities is obtained by distilling a spent reaction mixture, produced in beta lactam production, to produce a fraction containing the mixture of pivalic acid and impurities.

3. A process according to claim 1, wherein impurities contain an alkyl acetoacetate.

4. A process according to claim 1, wherein hydrolysis is carried out under strong acidic conditions.

5. A process according to claim 1, wherein step a) and step b) are carried out simultaneously by heating during step a).

6. A process for separating pivalic acid from a spent reaction mixture containing pivalic acid and an alkyl acetoacetate obtained in the production of a beta lactam, comprising
   (i) distilling the spent reaction mixture to produce a fraction containing a mixture of pivalic acid and an alkyl acetoacetate,
   (ii) degrading an alkyl acetoacetate in the fraction obtained in step (i) by hydrolysis to produce volatile fragments,
   (iii) isolating the pivalic acid.

7. A process for the production of pivaloyl chloride comprising
   a) hydrolyzing impurities in a mixture containing pivalic acid to produce volatile fragments;
   b) distilling off the volatile fragments;
   c) isolating the pivalic acid; and
   d) converting the pivalic acid obtained in step c) into pivaloyl chloride.

* * * * *